United States Patent [19]
Bennett et al.

[11] Patent Number: 6,117,847
[45] Date of Patent: Sep. 12, 2000

[54] OLIGONUCLEOTIDES FOR ENHANCED MODULATION OF PROTEIN KINASE C EXPRESSION

[75] Inventors: C. Frank Bennett, Carlsbad; Nicholas M. Dean, Olivenhain, both of Calif.

[73] Assignee: Isis Pharmaceuticals, Inc., Carlsbad, Calif.

[21] Appl. No.: 09/094,714

[22] Filed: Jun. 15, 1998

Related U.S. Application Data

[63] Continuation-in-part of application No. 08/664,336, Jun. 14, 1996, Pat. No. 5,922,686, which is a continuation-in-part of application No. 08/089,996, Jul. 9, 1993, Pat. No. 5,703,054, which is a continuation-in-part of application No. 07/852,852, Mar. 16, 1992, abandoned.

[51] Int. Cl.$^7$ .............................. A61K 31/70; C07H 21/00
[52] U.S. Cl. ............................ 514/44; 536/24.5; 435/375
[58] Field of Search .......................... 435/6, 375; 514/44; 536/24.31, 24.55

[56] References Cited

U.S. PATENT DOCUMENTS

| | | | |
|---|---|---|---|
| 4,511,713 | 4/1985 | Miller et al. ............................... | 536/27 |
| 4,806,463 | 2/1989 | Mattingly, III et al. ................ | 428/139 |
| 5,004,810 | 4/1991 | Draper ...................................... | 536/27 |
| 5,034,506 | 7/1991 | Summerton et al. ................... | 528/391 |
| 5,087,617 | 2/1992 | Smith ....................................... | 514/44 |
| 5,098,890 | 3/1992 | Gewirtz et al. .......................... | 514/44 |
| 5,135,917 | 8/1992 | Burch ....................................... | 514/44 |
| 5,138,045 | 8/1992 | Cook et al. ............................... | 536/27 |
| 5,166,195 | 11/1992 | Ecker ....................................... | 514/44 |
| 5,194,428 | 3/1993 | Agrawal et al. ......................... | 514/44 |
| 5,218,105 | 6/1993 | Cook et al. ........................... | 536/25.31 |
| 5,264,423 | 11/1993 | Cohen et al. ............................. | 514/44 |
| 5,276,019 | 1/1994 | Cohen et al. ............................. | 514/44 |
| 5,286,717 | 2/1994 | Cohen et al. ............................. | 514/44 |
| 5,378,825 | 1/1995 | Cook et al. ........................... | 536/25.34 |
| 5,459,255 | 10/1995 | Cook et al. ........................... | 536/27.13 |
| 5,539,082 | 7/1996 | Nielsen et al. .......................... | 530/300 |
| 5,591,721 | 1/1997 | Agrawal et al. ......................... | 514/44 |
| 5,620,963 | 4/1997 | Cook et al. ............................... | 514/44 |
| 5,681,747 | 10/1997 | Boggs et al. ............................. | 435/375 |
| 5,703,054 | 12/1997 | Bennet et al. ........................... | 514/44 |
| 5,744,460 | 4/1998 | Müller et al. ............................ | 514/44 |
| 5,922,686 | 7/1999 | Bennett et al. .......................... | 514/44 |

FOREIGN PATENT DOCUMENTS

| | | |
|---|---|---|
| 92/20823 | 11/1992 | WIPO . |
| 93/13121 | 7/1993 | WIPO . |
| 93/19203 | 9/1993 | WIPO . |
| 93/20101 | 10/1993 | WIPO . |
| 93/24510 | 12/1993 | WIPO . |
| 94/29455 | 12/1994 | WIPO . |
| WO 97/29780 | 8/1997 | WIPO . |

OTHER PUBLICATIONS

Gewirtz et al. Facilitating oligonucleotide delivery: Helping antisense deliver on its promise. Proc. Natl. Acad. Sci. USA 93: 3161–3163, Apr. 1996.

Stein. Keeping the biotechnology of antisense in context. Nature Biotechnol. 17: 209, Mar. 1999.

Ahmad, et al., "Antisense Expression of Protein Kinase Cα Inhibits the Growth and Tumorigenicity of Human Glioblastoma Cells", *Neurosurg.*, 35, 1994, 904–908.

Becker et al., "Differential expression of protein kinase C and cAmp–dependent protein kinase in normal human melanocytes and malignant melanomas", *Oncogene*, 1990, 5(8), 1133–1139 (Abstract Only).

Bioworld Today, Apr. 29, 1994, p. 3.

Cook, "Medicinal chemistry of antisense oligonucleotides–future opportunities", *Anti–Cancer Drug Des.*, 1991, 6, 585–607.

Sambrook, et al., Molecular Cloning. A Laboratory Manual, Cold Spring Harbor Laboratory Press, 1989, vol. 2, p. 10.59.

Uhlmann et al., "Antisense Oligonucleotides: A New Therapeutic Principle", *Chem. Rev.*, Jun. 1990, 90(4), 543–584.

Weinstein, et al., "Cancer Prevention: Recent Progress and Future Opportunities", *Cancer Res.*, (Suppl.) 51, 1991, 5080s–5085s.

1993 Catalog of Products for DNA Research, Glen Research, Sterling, VA, p. 21.

Bacher, et al., "Isolation and Characterization of PKC–L, a New Member of the Protein Kinase C–Related Gene Family Specifically Expressed in Lung, Skin and Heart", *Molecular and Cellular Biol.*, 11, 1191, 126–133.

Ballester and Rosen, Fate of Immunoprecipitable Protein Kinase C in $GH_3$ Cells Treated with Phorbol 12–Myristate 13–Acetate, *Journal of Biological Chemistry*, 260, 1985, 15194–15199.

Baxter, et al., "PKC–epsilon is involved in granulocyte–macrophage colong–stimulating factor signal transduction: Evidence from microphysiometry and antisense oligonucleotide experiments", *Biochemistry*, 31, 1992, 10950–10954.

Berkowitz, et al., "Synthesis of 1,2–Dihydro–1–(2–deoxy–β–D–Erythro–pentafuranosyl) – 2–Oxopyrazine 4–oxide, a potent analog of deoxyuridine", *J. Medicinal Chemistry*, 16(2), 1973, 813–814.

Borek, et al., "Long Chain (sphingoid) Bases Inhibit Multistage Carcinogenesis in Mouse C3H/10T1/2 Cells Treated with Radiation and Phorbol 12–Myristate 13–Acetate", *Proc. Natl. Acad. Sci.*, 88, 1991, 1953–1957.

(List continued on next page.)

*Primary Examiner*—Robert A. Schwartzman
*Assistant Examiner*—Thomas G. Larson
*Attorney, Agent, or Firm*—Woodcock Washburn Kurtz Mackiewicz & Norris LLP

[57] ABSTRACT

Compositions and methods are provided for modulating the expression of protein kinase C. Oligonucleotides are provided which are targeted to nucleic acids encoding PKC. The oligonucleotides are from 5 to 50 nucleotides in length and in one referred embodiment are from 12 to 18 nucleotides in length. The oligonucleotides may be chimeric oligonucleotides and in a preferred embodiment comprise at least one 2'-O-methoxyethyl modification. Pharmaceutical compositions comprising the oligonucleotides of the invention are also provided. Methods of inhibiting protein kinase C expression and methods of treating conditions associated with expression of protein kinase C using oligonucleotides of the invention are disclosed.

35 Claims, No Drawings

OTHER PUBLICATIONS

Coussens, et al., "Multiple, Distinct Forms of Bovine and Human Protein Kinase C Suggest Diversity in Cellular Signaling Pathways", *Science*, 233, 1986, 859–866.

Endo, et al., "Cell Membrane Signaling as Target in Cancer Therapy: Inhibitory Effect of N,N–Dimethyl and N,N,N–Trimethyl Sphingosine Derivatives on in Vitro and in Vivo Growth of Human Tumor Cells in Nude Mice", *Cancer Research*, 51, 1991, 1613–1618.

Farese, et al., "Antisense DNA downregulates protein kinase C isozymes (beta and alpha) and insulin–stimulated 2–deoxyglucose uptake in rat adipocytes", *Antisense, Res. Dev.*, 1(1), 1991, 35–42.

Finkenzeller, et al., "Sequence of Human Protein Kinase C α", *Nucl. Acids Res.*, 18, 1990, 2183.

Gescher and Dale, "Protein Kinase C—A Novel Target for Rational Anti–Cancer Drug Design?" *Anti–Cancer Drug Design*, 4, 1989, 93–105.

Godson, et al., "Inhibition of Expression of Protein Kinase C α By Antisense cDNA Inhibits Phorbol Ester–Mediated Arachidonate Release", *J. Biol. Chem.*, 268, 1993, 11946–11950.

Hackh's Chemical Dictionary, Grant, et al., Ed., McGraw–Hill Book Company, New York, p. 312.

Hegemann and Mahrle, *Pharmacology of the Skin*, H. Mukhtar, Ed., pp. 357–368, CRC Press, Boca Raton, FL, 1992.

Hidaka and Hagiwara, "Pharmacology of the Isoquinoline Sulfonamide Protein Kinase C Inhibitors", *Trends in Pharm Sci.*, 8, 1987, 162–164.

Kawasaki, A.M. et al., "Synthesis and Biophysical Studies of 2'–dRibo–2'–F Modified Oligonucleotides", *Conf. On Nucleic Acid Therapeutics*, Clearwater, FL, Jan. 13–16, 1991, 10 pages.

Krug, et al., "Evidence for Increased Synthesis as well as Increased Degradation of Protein Kinase C After Treatment of Human Osteosarcoma Cells with Phorbol Ester", *J. Biol. Chem.*, 262, 1987, 11852–11856.

Kubo, et al., "Primary Structures of Human Protein Kinase CβI and βII Differ Only in their C–Terminal Sequences", *FEBS Lett.* 223, 1987, 138–142.

Maier, et al., "An oligomer targeted against protein kinase C alpha prevents interleukin–1 alpha induction of cyclooxygenase expression in human endothelial cells", *Exp. Cell. Res.*, 205(1), 1993, 52–58.

Marcus–Sekura, "Techniques for Using Antisense Oligodeoxyribonucleotides to Study Gene Expression", *Analytical Biochemistry*, 172, 1988, 289–295.

Nielsen, et al., "Sequence–Selective Recognition of DNA by Strand Displacement with a Thymine–Substituted Polyamide", *Science*, 254, 1991, 1497–1500.

Nishizuka, "The Molecular Heterogeneity of Protein Kinase C and Its Implications for Cellular Regulation", *Nature*, 334, 1988, 661–665.

Osada, et al., "A Phorbol Ester Receptor/Protein Kinase nPKCη, a New Member of the Protein Kinase C Family Predominantly Expressed in Lung and Skin", *J. Biol. Chem.*, 265, 1990, 22434–22440.

Parker, et al., "The Complete Primary Structure of Protein Kinase C–the Major Phorbol Ester Receptor", *Science*, 233, 1986, 853–866.

Rothenberg, et al., "Oligodeoxynucleotides as Anti–Sense Inhibitors of Gene Expression: Therapeutic Implications", *J. Natl. Cancer Inst.*, 1989, 81, 1539–1544.

Sakanoue, et al., "Protein Kinase C Activity as Marker for Colorectal Cancer", *Int. J. Cancer*, 48, 1991, 803–806.

Standaert, et al., 1991, J. Cellular Biochem., (Keystone Symposia on Molecular and Cellular Biology), Jan. 18–25), Suppl. 15B, p. 26, abstract CA 211.

Watson, et al., 1987, in: Molecular Biology of the Gene, Fourth Edition, Benjamin/Cummings Publishing Company, Menlo Park, CA p. 241.

Webster's II New Riverside University Dictionary, Soulkkanov, et al., Eds., 1984, Houghton Mifflin Company, Boston, MA, p. 68.

Young, et al., "Down–Regulation of Protein Kinase C is Due to an Increased Rate of Degradation", *Biochem. J*, 244, 1987, 775–779.

Zon, "Oligonucleotide Analogues as Potential Chemotherapeutic Agents", *Pharmaceutical Res.*, 5, 1988, 539–549.

Brandt, et al., "Distinct Patterns of Expression of Different Protein Kinase C mRNA's in Rat Tissue", *Cell*, 49, 57–63.

Simons, et al., "Antisense c–myb oligonucleotides inhibit intimal arterial smooth muscle cell accumulation in vivo", *Nature*, 359, 1992, 67–70.

Greenberg in Current Protocols in Molecular Biology, Ausubel, et al., Eds., John Wiley & Sons, NY, 1987.

Berge, S.M. et al., "Pharmaceutical Salts", *J. Pharm. Sci.*, 1977, 66, 1–19.

Chiang, M.Y. et al., "Antisense Oligonucleotides Inhibit Intercellular Adhesion Molecule 1 Expression by Two Distinct Mechanisms", *J. Biol. Chem.*, 1991, 266, 18162–18171.

Chonn, A. et al., "Recent advances in liposomal drug–delivery systems", *Curr. Op. in Biotechnology*, 1995, 6, 698–708.

Crooke, S.T. et al., "Pharmacokinetic Properties of Several Novel Oligonucleotide Analogs in mice", *J. Pharmacol. Exp. Therapeutics*, 1996, 277, 923–937.

Dean, N.M. et al., "Inhibition of protein Kinase C–α Expression in Human A549 Cells by Antisense Oligonucleotides Inhibits Induction of Intercellular Adhesion Molecule 1 (ICAM–1 mRNA by Phorbol Esters", *J. Biol. Chem.*, 1994, 269, 16416–15424.

De Mesmaeker, A. et al., "Antisense Oligonucleotides", *Ace. Chem. Res.*, 1995, 28, 366–374.

Gebeyehu, G. et al., "Novel bitinylated nucleotide—analogs for labeling and colorimetric detection of DNA", *Nucl. Acids Res.*, 1987, 15, 4513–4534.

Kabanov, A.V., "A new class of antivirals: antisense olgonucleotides combined with hydrophobic substituent effectively inhibit influenza virus reproduction and synthesis of virus–specific proteins in MDCK cells", *FEBS Letts.*, 1990, 259, 327–330.

Kawasaki, A.M. et al., "Uniformly Modified 2'–Deoxy–2'–fluoro Phosphorothioate Oligonucleotides as Nuclease–Resistant Antisense Compounds with High Affinity Specificity for RNA Targets", *J. Med. Chem.*, 1993, 831–841.

Kornberg, A., *DNA Replication*, W.H. Freeman and Co., San Francisco, 1980, 75–77.

Lee, V.H.L. et al., "Mucosal Penetration Enhancers For Facilitation of Peptide and Protein Drug Absorption", *Crit. Rev. Ther. Drug Carrier Systems*, 1991, 8, 91–192.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Manoharan M. et al., "Cholic Acid–Oligonucliotide Conjugates for Antisense Applications", *Bioorganic Med. Chem. Letts.*, 1994, 4, 1053–1060.

Manoharan, M. et al., "Chemical Modifications to Improve Uptake and Bioavailability of Antisense Oligonucleotides", *Annals NY Acad. Sciences*, 1992, 660, 306–309.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan, M. et al., "Lipidic Nucleic Acids", *Tetrahedron Letts.*, 1995, 36, 3651–3654.

Manoharan M. et al., "Oligonucleotide Conjugates: Alteration of the Pharmacokinetic Properties of Antisense Agents", *Nucleosides and Nucleotides*, 1995, 14, 969–973.

Martin, P., "Ein neuer Zugang zu 2'-O-Alkylribonucleosiden und Eigenschaften deren Oligonucleotide", *Helvitica Chemica Acta*, 1995, 78, 486–504.

McGraw, K. et al., "Antisense oligonucleotide inhibitors of isozymes of protein kinase C: in vitro and in vivo activity and clinical development as anti–cancer therapeutics", *Anti–Cancer Drug Des.*, 1997, 12, 315–326.

Mishra, R.K. et al., "Improved leishmanicidal effect of phosphorotioate antisense oligonucleotides by LDL–mediated delivery", *Biochim. Et Biophysica*, 1995, 1264, 229–237.

Nishizuka, Y., "Protein kinase C and lipid signaling for sustained cellular responses", *FASEB J.*, 1995, 9, 484–496.

Oberhauser, B. et al., "Effective incorporation of 2'-O-methyl–oligonucleotides into liposomes and enhanced cell association through modification with thiocholesterol", *Nucl. Acids Res.*, 1992, 20, 533–538.

Saison–Behmoaras, T. et al., "Short modified antisense oligonucleotides directed against Ha–ras point mutation induce selective cleavage of the mRNA and inhibit T24 cells proliferation", *EMBO J.*, 1991, 10, 1111–1118.

Shea, R.G. et al., "Synthesis, hybridization properties and antiviral activity of lipid–oligodeoxynucletide conjugates", *Nucl. Acids Res.*, 1990, 18, 3777–3783.

Stewart, A., "Antisense against protein kinase C–α mRNA makes sense for cancer therapy?", *Molecular Medicine Today*, 1997, 3(8), 324.

Svinarchuk, F.P. et al., "Inhibition of HIV proliferation in MT–4 Cells by antisense oligonucleotide conjugated to lipophilic groups", *Biochimie*, 1993, 79, 49–54.

OLIGONUCLEOTIDES FOR ENHANCED MODULATION OF PROTEIN KINASE C EXPRESSION

CROSS REFERENCE TO RELATED APPLICATIONS

This application is a continuation-in-part of U.S. patent application Ser. No. 08/664,336 filed Jun. 14, 1996, now U.S. Pat. No. 5,922,686, which is a continuation-in-part of U.S. patent application Ser. No. 08/089,996, filed Jul. 9, 1993, which issued on Dec. 30, 1997 as U.S. Pat. No. 5,703,054, which in turn is a continuation-in-part of U.S. patent application Ser. No. 07/852,852 filed Mar. 16, 1992, now abandoned.

FIELD OF THE INVENTION

This invention relates to compositions and methods for modulation of the expression of protein kinase C. In particular, this invention relates to antisense oligonucleotides specifically hybridizable with nucleic acids encoding protein kinase C. These oligonucleotides have been found to modulate the expression of protein kinase C. These compositions and methods can be used diagnostically or therapeutically.

BACKGROUND OF THE INVENTION

The phosphorylation of proteins plays a key role in the transduction of extracellular signals into the cell. The enzymes, called kinases, which effect such phosphorylations are targets for the action of growth factors, hormones, and other agents involved in cellular metabolism, proliferation and differentiation. One of the major signal transduction pathways involves the enzyme protein kinase C (PKC), which is known to have a critical influence on cell proliferation and differentiation. PKC is activated by diacylglycerols (DAGs), which are metabolites released in signal transduction.

Interest in PKC was stimulated by the finding that PKC is the major, and perhaps only, cellular receptor through which a class of tumor-promoting agents called phorbol esters exert their pleiotropic effects on cells (Gescher et al., *Anti-Cancer Drug Design* 4:93–105 (1989)). Phorbols capable of tumor production can mimic the effect of DAG in activating PKC, suggesting that these tumor promoters act through PKC and that activation of this enzyme is at least partially responsible for the resulting tumorigenesis (Parker et al., *Science* 233:853–866 (1986)).

Experimental evidence indicates that PKC plays a role in growth control in colon cancer. It is believed that specific bacteria in the intestinal tract convert lipids to DAG, thus activating PKC and altering cell proliferation. This may explain the correlation between high dietary fat and colon cancer (Weinstein, *Cancer Res. (Suppl.)* 51:5080s–5085s (1991)). It has also been demonstrated that a greater proportion of the PKC in the colonic mucosa of patients with colorectal cancer is in an activated state compared to that of patients without cancer (Sakanoue et al., *Int. J Cancer* 48:803–806 (1991)).

Increased tumorigenicity is also correlated with overexpression of PKC in cultured cells inoculated into nude mice. A mutant form of PKC induces highly malignant tumor cells with increased metastatic potential. Sphingosine and related inhibitors of PKC activity have been shown to inhibit tumor cell growth and radiation-induced transformation in vivo (Endo et al., *Cancer Research* 51:1613–1618 (1991); Borek et al., *Proc. Natl. Acad. Sci.* 88:1953–1957 (1991)). A number of experimental or clinically useful anti-cancer drugs show modulatory effects on PKC. Therefore, inhibitors of PKC may be important cancer-preventive or therapeutic agents. PKC has been suggested as a plausible target for more rational design of conventional anti-cancer drugs (Gescher, A. and Dale, I. L., *Anti-Cancer Drug Design,* 4:93–105 (1989)).

Experiments also indicate that PKC plays an important role in the pathophysiology of hyperproliferative skin disorders such as psoriasis and skin cancer. Psoriasis is characterized by inflammation and hyperproliferation of the epidermis and decreased differentiation of cells. Various studies indicate a role for PKC in causing these symptoms. PKC stimulation in cultured keratinocytes can be shown to cause hyperproliferation. Inflammation can be induced by phorbol esters and is regulated by PKC. DAG is implicated in the involvement of PKC in dermatological diseases, and is formed to an increased extent in psoriatic lesions.

Inhibitors of PKC have been shown to have both antiproliferative and anti-inflammatory effects in vitro. Some anti-psoriasis drugs, such as cyclosporine A and anthralin, have been shown to inhibit PKC. Inhibition of PKC has been suggested as a therapeutic approach to the treatment of psoriasis (Hegemann, L. and G. Mahrle, *Pharmacology of the Skin,* H. Mukhtar, ed., p. 357–368, CRC Press, Boca Raton, Fla., 1992).

The oligonucleotides of the invention are believed to be useful in the therapeutic treatment of diseases associated with PKC. Such diseases include hyperproliferative and inflammatory conditions including psoriasis, tumors and cancers such as, for example, glioblastoma, bladder cancer, skin cancer, breast cancer, lung cancer and colon cancer.

PKC is not a single enzyme, but a family of enzymes. At the present time at least ten isoforms (isozymes) of PKC have been identified: the "conventional" isoforms $\alpha$, $\beta$, and $\gamma$, the "novel" isoforms $\delta$, $\epsilon$, $\eta$, $\theta$ and $\mu$, and the "atypical" isoforms $\zeta$ and $\lambda(\iota)$. These isozymes have distinct patterns of tissue and organ localization (see Nishizuka, *FASEB J* 9:484–496 (1995) for review) and may serve different physiological functions.

It is presently believed that different PKC isozymes may be involved in various disease processes depending on the organ or tissue in which they are expressed. For example, in psoriatic lesions there is an alteration in the ratio between PKC-$\alpha$ and PKC-$\beta$, with preferential loss of PKC-$\beta$ compared to normal skin (Hegemann, L. and G. Mahrle, *Pharmacology of the Skin,* H. Mukhtar, ed., p. 357–368, CRC Press, Boca Raton, Fla., 1992).

Although numerous compounds have been identified as PKC inhibitors (see Hidaka and Hagiwara, *Trends in Pharm. Sci.* 8:162–164 (1987) for review), few have been found which inhibit PKC specifically. While the quinoline sulfonamide derivatives such as 1-(5-isoquinolinesulfonyl)-2-methylpiperazine (H-7) inhibit PKC at micromolar concentrations, they exhibit similar enzyme inhibition kinetics for PKC and the cAMP-dependent and cGMP-dependent protein kinases. Staurosporine, an alkaloid product of Streptomyces sp., and its analogs, are the most potent in vitro inhibitors of PKC identified to date. However, they exhibit only limited selectivity among different protein kinases (Gescher, *Anti-Cancer Drug Design* 4:93–105 (1989)). Certain ceramides and sphingosine derivatives have been shown to have PKC inhibitory activity and to have promise for therapeutic uses, however, there remains a long-felt need for specific inhibitors of the enzymes.

There is also a desire to inhibit specific PKC isozymes, both as a research tool and in diagnosis and treatment of diseases which may be associated with particular isozymes.

Godson et al. (*J Biol. Chem.* 268:11946–11950 (1993)) disclosed use of stable transfection of antisense PKC-$\alpha$ cDNA in cytomegalovirus promotor-based expression vectors to specifically decrease expression of PKC-α protein by approximately 70%. It was demonstrated that this inhibition caused a loss of phospholipase $A_2$-mediated arachidonic acid release in response to the phorbol ester PMA. Attempts by the same researchers at inhibiting PKC activity with oligodeoxynucleotides were ultimately unsuccessful due to degradation of oligonucleotides. Ahmad et al. disclose that transfection of the human glioblastoma cell line, U-87, with vectors expressing antisense RNA to PKC-α inhibits growth of the glioblastoma cells in vitro and in vivo (Ahmad et al., *Neurosurg.* 35:904–908 (1994)). Diaz-Meco Conde et al. disclose a peptide corresponding to the pseudo-substrate region of PKC-ζ and oligonucleotides antisense to this isozyme (WO Application 93/20101). Alvaro et al. have identified a novel mutant form of PKC associated with tumors and disclose oligonucleotide sequences complementary to the mutant form (WO Application 94/29455).

SUMMARY OF THE INVENTION

In accordance with the present invention, oligonucleotides of reduced length are provided that are specifically hybridizable with a nucleic acid that encodes PKC-α and are capable of inhibiting PKC-α expression. This relationship is commonly denominated as "antisense". The oligonucleotides typically contain one or more modifications to improve oligonucleotide stability, binding affinity or potency and may be chimeric oligonucleotides. In a preferred embodiment the oligonucleotides comprise at least one 2'-O-methoxyethyl modification. The oligonucleotides are less than about 19 nucleotides long and in one embodiment are fifteen nucleotides long (15-mers). These oligonucleotides are believed to be useful therapeutically, diagnostically and as research reagents and are believed to be particularly useful for their ability to decrease the expression of PKC in an isoform-specific manner.

Also provided are methods for modulating the expression of PKC-α using the oligonucleotides of the invention. These methods are believed to be useful both therapeutically and diagnostically as a consequence of the relationship between PKC-α and inflammation and hyperproliferation. Other aspects of the invention are directed to methods for diagnostics and treatment of conditions associated with PKC-α.

DETAILED DESCRIPTION OF THE INVENTION

The present invention employs oligonucleotides for use in inhibiting the function of nucleic acid molecules encoding PKC, ultimately modulating the amount of PKC produced. This is accomplished by providing oligonucleotides which specifically hybridize with nucleic acids, preferably mRNA, encoding PKC.

This relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding PKC, such as, for example, a PKC gene or mRNA expressed from a PKC gene. PKC mRNAs are presently the preferred targets. The targeting process also includes determination of a site or sites within the nucleic acid sequence for the oligonucleotide interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding PKC, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'-UTR), known in the art to refer to the portion of an mRNA in the 5' direction from the translation initiation codon, and thus including nucleotides between the 5' cap site and the translation initiation codon of an mRNA or corresponding nucleotides on the gene) and the 3' untranslated region (3'-UTR), known in the art to refer to the portion of an mRNA in the 3' direction from the translation termination codon, and thus including nucleotides between the translation termination codon and 3' end of an mRNA or corresponding nucleotides on the gene). mRNA splice sites may also be preferred target regions, and are particularly useful in situations where aberrant splicing is implicated in disease, or where an overproduction of a particular mRNA splice product is implicated in disease. Aberrant fusion junctions due to rearrangements or deletions may also be preferred targets.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more MRNA species, and catalytic activity which may be engaged in by the RNA.

The overall effect of interference with mRNA function is modulation of PKC expression. In the context of this invention "modulation" means either inhibition or stimulation. Inhibition of PKC gene expression is presently the preferred form of modulation. This modulation can be measured in ways which are routine in the art, for example by Northern blot assay of mRNA expression as taught in the examples of the instant application or by Western blot or ELISA assay of protein expression. Effects on cell proliferation or tumor cell growth can also be measured, as taught in the examples of the instant application.

The oligonucleotides of this invention can be used in diagnostics, therapeutics, prophylaxis, and as research reagents and in kits. Since the oligonucleotides of this invention hybridize to nucleic acids encoding PKC, sandwich, colorimetric and other assays can easily be constructed to exploit this fact. Furthermore, since the oligonucleotides of this invention hybridize specifically to nucleic acids encoding particular isozymes of PKC, such assays can be devised for screening of cells and tissues for particular PKC isozymes. Such assays can be utilized for diagnosis of diseases associated with various PKC forms. Provision of means for detecting hybridization of oligonucleotide with a PKC gene or mRNA can routinely be accomplished. Such provision may include enzyme conjugation, radiolabelling or any other suitable detection systems. Kits for detecting the presence or absence of PKC may also be B prepared.

The present invention is also suitable for diagnosing abnormal proliferative states in tissue or other samples from patients suspected of having a hyperproliferative disease such as cancer or psoriasis. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal. Similarly, the present invention can be used to distinguish PKC-associated tumors, particularly tumors associated with PKC-α, from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates and those with $CH_2-NH-O-CH_2$, $CH_2-N(CH_3)-O-CH_2$ (known as a methylene(methylimino) or MMI backbone), $CH_2-O-N(CH_3)-CH_2$, $CH_2-N(CH_3)-N(CH_3)-CH_2$ and $O-N(CH_3)-CH_2-CH_2$ backbones, wherein the native phosphodiester backbone is represented as $O-P-O-CH$). Also preferred are oligonucleotides having morpholino backbone structures (Summerton and Weller, U.S. Pat. No. 5,034,506). Further preferred are oligonucleotides with $NR-C(*)-CH_2-CH_2$, $CH_2-NR-C(*)-CH_2$, $CH_2-CH_2-NR-C(*)$, $C(*)-NR-CH_2-CH_2$ and $CH_2-C(*)-NR-CH_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science*, 1991, 254, 1497; U.S. Pat. No. 5,539,082). Other preferred modified oligonucleotides may contain one or more substituted sugar moieties comprising one of the following at the 2' position: OH, SH, $SCH_3$, F, OCN, $OCH_3$, $OCH_3$, $OCH_3O$ $(CH_2)nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-O-methoxyethyl (which can be written as 2'-O—$CH_2CH_2OCH_3$, and is also known in the art as 2'-O-(2-methoxyethyl) or 2'-methoxyethoxy) (Martin et al., Helv. Chim. Acta, 1995, 78,486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of the 5' terminal nucleotide. Oligonucleotides may also have sugar mimetics such as cyclobutyls in place of the pentofuranosyl group.

The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-methylcytosine, 5-hydroxymethylcytosine (HMC), glycosyl HMC and gentiobiosyl HMC, as well synthetic nucleobases, e.g., 5-bromouracil, 5-hydroxymethyluracil, 8-azaguanine, 7-deazaguanine, $N^6$(6-aminohexyl)adenine and 2,6-diaminopurine (Komberg, A., DNA Replication, 1974, W. H. Freeman & Co., San Francisco, 1974, pp. 75–77; Gebeyehu, G., et al., Nucleic Acids Res., 1987, 15, 4513).

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The $N^6$ position of a purine nucleobase may also be utilized to link a lipophilic moiety to an oligonucleotide of the invention (Gebeyehu, G., et al., Nucleic Acids Res., 1987, 15, 4513). Such lipophilic moieties include but are not limited to a cholesteryl moiety (Letsinger et al., Proc. Natl. Acad. Sci. USA, 1989, 86, 6553), cholic acid (Manoharan et al., Bioorg Med. Chem. Let., 1994, 4, 1053), a thioether, e.g., hexyl-S-tritylthiol (Manoharan et al., Ann. N.Y. Acad. Sci., 1992, 660, 306; Manoharan et al., Bioorg Med Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995,1264, 229), or an octadecylamine or hexylamino-carbonyl-oxycholesterol moiety (Crooke et al., J. Pharmacol. Exp. Ther., 1996, 277, 923). Oligonucleotides comprising lipophilic moieties, and methods for preparing such oligonucleotides, as disclosed in U.S. Pat. No. 5,138,045, 5,218,105 and 5,459,255, the contents of which are hereby incorporated by reference in their entirety.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3'"wings") are modified to have greater affinity for the target RNA molecule but are unable to support nuclease activity (e.g., 2'-fluoro- or 2'-O-methoxyethyl- substituted). Other chimeras include "wingmers," also known in the art as "hemimers," that is, oligonucleotides with two distinct regions. In a preferred example of a wingiener, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa.

In one embodiment, the oligonucleotides of the present invention contain a 2'-O-methoxyethyl (2'-O—$CH_2CH_2OCH_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (-O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred. Through use of such modifications, active oligonucleotides have been identified which are shorter than conventional "first generation" oligonucleotides active against PKC. Oligonucleotides in accordance with this invention are from 5 to 50 nucleotides in length, more preferably 12 to 25, more preferably 12 to 20, most preferably 12 to 18. In one highly preferred embodiment the oligonucleotides are 15 nucleotides in length. In the context of this invention it is understood that oligonucleotides in accordance with this invention encompass non-naturally occurring oligomers as hereinbefore described, having from 5 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., Helv. Chim. Acta, 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids.

"Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.*, 1977, 66:1, which is incorporated herein by reference in its entirety).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl) phosphate) derivatives according to the methods disclosed in WO 93/24510 to Gosselin et al., published Dec. 9, 1993, which is incorporated herein by reference in its entirety.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, ie., fatty acids, bile salts, chelating agents, surfactants and non-surfactants (Lee et al., *Critical Reviews in Therapeutic Drug Carrier Systems*, 1991, 8:91–192; Muranishi, *Critical Reviews in Therapeutic Drug Carrier Systems*, 1990, 7:1). One or more penetration enhancers from one or more of these broad categories may be included. Compositions comprising oligonucleotides and penetration enhancers are disclosed in co-pending U.S. patent application Ser. No. 08/886,829 to Teng et al., filed Jul. 1, 1997, which is herein incorporated by reference in its entirety.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.*, 1995, 6, 698). Liposomal antisense compositions are prepared according to the disclosure of co-pending U.S. patent application Ser. No. 08/961,469 to Hardee et al., filed Oct. 31, 1997, incorporated herein by reference in its entirety.

The pharmaceutical compositions of the present invention may be administered in a number of ways depending upon whether local or systemic treatment is desired and upon the area to be treated. Administration may be topical (including ophthalmic, vaginal, rectal, intranasal, epidermal and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. For oral administration, it has been found that oligonucleotides with at least one 2'-substituted ribonucleotide are particularly useful because of their absorption and distribution characteristics. U.S. Pat. No. 5,591,721 issued to Agrawal et al. Oligonucleotides with at least one 2'-O-methoxyethyl modification are believed to be particularly useful for oral administration. Modes of administering oligonucleotides are disclosed in co-pending U.S. patent application Ser. No. 08/961,469 to Hardee et al., filed Oct. 31, 1997, herein incorporated by reference in its entirety.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Thus, in the context of this invention, by "therapeutically effective amount" is meant the amount of the compound which is required to have a therapeutic effect on the treated mammal. This amount, which will be apparent to the skilled artisan, will depend upon the type of mammal, the age and weight of the mammal, the type of disease to be treated, perhaps even the gender of the mammal, and other factors which are routinely taken into consideration when treating a mammal with a disease. A therapeutic effect is assessed in the mammal by measuring the effect of the compound on the disease state in the animal. For example, if the disease to be treated is psoriasis, a reduction or ablation of the skin plaque is an indication that the administered dose has a therapeutic effect. Similarly, in mammals being treated for cancer, therapeutic effects are assessed by measuring the rate of growth or the size of the tumor, or by measuring the production of compounds such as cytokines, production of which is an indication of the progress or regression of the tumor.

We have previously identified oligonucleotides which are able to inhibit PKC expression in vitro, in animals and in human xenografts in animals. One such oligonucleotide, ISIS 3521, is presently in clinical trials and has shown antitumor activity in patients with ovarian and lung cancer and lymphoma that were refractory to standard cancer chemotherapy. McGraw et al., 1997, Anti-Cancer Drug Design 12:315–326; Stewart, A., 1997, Molecular Medicine Today, August 1997, p. 324. This compound is a 20-mer (i.e., 20 nucleotides in length) phosphorothioate oligodeoxynucleotide. We have now found that antisense oligonucleotides of reduced length can effectively inhibit expression of PKC, and thus exhibit enhanced activity on a per-gram basis.

The following examples illustrate the present invention and are not intended to limit the same.

EXAMPLES

Example 1

Oligonucleotide synthesis

Unmodified oligodeoxynucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of $^3$H-1,2-benzodithiole-3-one 1,1 -dioxide in acetonitrile for the stepwise thiation of the phosphite linkages. The thiation cycle wait step was increased to 68 seconds and was followed by the capping step.

2'-methoxy oligonucleotides were synthesized using 2'-methoxy β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al., *J. Med. Chem.* 1993, 36, 831. Briefly, the protected nucleoside $N^6$-benzoyl-2'-deoxy-2'-fluoroadenosine was synthesized utilizing commercially available 9-β-D-arabinofuranosyladenine as starting material and by modifying literature procedures whereby the 2'-"-fluoro atom is introduced by a $S_N2$-displacement of a 2'-β-O-trifyl group. Thus $N^6$-benzoyl-9-β-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl-(DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a literature procedure in which 2, 2'-anhydro-1-β-D-arabinofuranosyluracil was treated with 70% hydrogen fluoride-pyridine. Standard procedures were used to obtain the 5'-DMT and 5'-DMT-3'-phosphoramidites. 2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3' phosphoramidites.

Oligonucleotides having methylene(methylimino) backbones are synthesized according to U.S. Pat. No. 5,378,825, which is coassigned to the assignee of the present invention and is incorporated herein in its entirety. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al., *Acc. Chem. Res.*, 1995, 28, 366. The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al., *Science* 1991, 254, 1497.

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylanide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.*, 1991, 266, 18162. Results obtained with HPLC-purified material were similar to those obtained with non-HPLC purified material.

Oligonucleotides having 2'-O—CH$_2$CH$_2$OCH$_3$ modified nucleotides were synthesized according to the method of Martin. *Helv. Chim. Acta* 1995, 78,486–504. All 2'-O—CH$_2$CH$_2$OCH$_3$-cytosines were 5-methyl cytosines, synthesized as follows:

5-Methyl cytosine monomers:
2,2'-Anhydro[1-(β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with _EtOAc/Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N[4]-Benzoyl-2'-O-methoxyethyl-5'-O-dimethoxytrityl-5-methylcytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

N[4]-Benzoyl-2'-O-methoxyethyl-5'-O-dimethoxytrityl-5-methylcytidine-3'-amidite:

N[4]-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound.

Example 2

Cell culture and treatment with phorbol esters and oligonucleotides

PKC protein half-lives have been reported to vary from 6.7 hours to over 24 hours (Young et al., *Biochem. J.* 244:775–779 (1987); Ballester et al., *J. Biol. Chem.* 260:15194–15199 (1985)). These long half-lives make inhibiting steady-state levels of PKC-α an unwieldy approach when screening antisense oligonucleotides, due to the long incubation times which would be required. We have therefore made use of the ability of phorbol esters to reversibly lower intracellular levels of PKC. Treatment of cells with phorbol esters causes an initial activation of kinase activity, followed by a down-regulation of PKC. For PKC-α this down-regulation has been shown to be a direct consequence of an increased rate of proteolysis of the kinase with no apparent change in synthetic rate.

We determined that in human lung carcinoma (A549) cells, treatment with the phorbol ester 12,13-dibutyrate (PDBu), using a modification of the method of Krug et al., (Krug et al., *J. Biol. Chem.* 262:11852–11856 (1987)) lowered cellular levels of PKC-α, without affecting PKC-α mRNA levels, and that this effect was reversible. The basis of the assay to screen for potency of oligonucleotides targeting PKC-α is to initially lower PKC-α protein levels by chronic treatment with PDBu, remove PDBu by extensively washing the cells (hence allowing the cells to synthesize fresh PKC-α protein), and incubate the cells with oligonucleotides intended to inhibit the resynthesis of new PKC-α protein.

Procedure: A549 cells (obtained from the American Type Culture Collection, Bethesda Md.) were grown to confluence in 6-well plates (Falcon Labware, Lincoln Park, N.J.) in Dulbecco's modified Eagle's medium (DME) containing 1 g glucose/liter and 10% fetal calf serum (FCS, Irvine Scientific, Santa Ana, Calif.). Cells were treated with 500 nM PDBu (Sigma Chem. Co., St. Louis, Mo.) for 12–16 hours (overnight). Cells were then washed three times in DME at 37° C.

Example 3

Northern blot analysis of PKC mRNA levels after treatment of A549 cells with antisense oligonucleotides of reduced length A549 cells were treated with phosphorothioate oligonucleotides at 200 nM for four hours in the presence of the cationic lipids DOTMA/DOPE, washed and allowed to recover for an additional 20 hours. Total RNA was extracted and 20 μg of each was resolved on 1.2% gels and transferred to nylon membranes. These blots were probed with a $^{32}P$ radiolabeled PKC-α cDNA probe and then stripped and reprobed with a radiolabeled G3PDH probe to confirm equal RNA loading. Each oligonucleotide (3520, 3521,3522 and 3527) was used in duplicate. The two major PKC-α transcripts (8.5 kb and 4.0 kb) were examined and quantified with a PhosphorImager (Molecular Dynamics, Sunnyvale Calif.).

A series of 15-mer oligonucleotides targeted to human PKC-α were designed using the cDNA sequence published by Finkenzeller et al., *Nucl. Acids Res.* 18:2183 (1990); Genbank accession number X52479; incorporated herein as SEQ ID NO:48. These were designed as chimeric oligonucleotides of the type sometimes referred to in the art as "hemimers" or "wingmers," with the first 8 nucleotides at the 5' end being 2'-deoxynucleotides and the remaining 7 nucleotides being 2'-O-methoxyethyl. The intersugar linkages are phosphorothioates throughout and all 2'-O-methoxyethylcytidines have 5-methyl-cytosine bases (5-meC). These compounds are shown in Table 1. Nucleotides shown in bold are 2'-O-methoxyethyl. Activity is expressed as percent inhibition of PKC-α mRNA levels compared to control (no oligo). Nucleotide numbers in "Target site" column correspond to those of SEQ ID NO:48 (Genbank accession number x52479).

TABLE 1

15-mers targeted to PKC-α:

| ISIS # | Sequence | Target region | Target site | %Inhib'n | SEQ ID NO: |
|---|---|---|---|---|---|
| 14095 | ACCACCTCTTGCTCC | 5'UTR | 0001–0015 | 8 | 1 |
| 14096 | TGAAGAAGCGCGCGA | Coding | 0146–0160 | 68 | 2 |

TABLE 1-continued 15-mers targeted to PKC-α:

| ISIS # | Sequence | Target region | Target site | %Inhib'n | SEQ ID NO: |
|---|---|---|---|---|---|
| 14097 | TTGAACTTGTGCTTG | Coding | 0327–0341 | 56 | 3 |
| 14098 | GCCCCCTCTTCTCAG | Coding | 0494–0508 | 2 | 4 |
| 14099 | TTCATTCTTGGGATC | Coding | 0634–0648 | 0 | 5 |
| 14100 | CATCCACTGGCCGGC | Coding | 0834–0848 | 16 | 6 |
| 14101 | TGCCTGAGTTCCATG | Coding | 0921–0935 | 0 | 7 |
| 14102 | CAGGATTTTGATTGC | Coding | 1123–1137 | 0 | 8 |
| 14103 | TCCGATGGAAATCTC | Coding | 1363–1377 | 30 | 9 |
| 14104 | ACTCCATCCATCATG | Coding | 1491–1505 | 0 | 10 |
| 14105 | GCATGCTCTCTCACG | Coding | 1797–1811 | 33 | 11 |
| 14106 | CGCTGGTGAGTTTCA | Stop/3'UTR | 2044–2058 | 19 | 12 |
| 14107 | AGGATTCACTTCCAC | 3'UTR | 2096–2110 | 6 | 13 |
| 14108 | CCGTGGCCTTAAAAT | 3'UTR | 2121–2135 | 22 | 14 |
| 14109 | CCCTACAATTTTCAG | 3'UTR | 2161–2175 | 4 | 15 |
| 14110 | GAGACCCTGAACAGT | 3'UTR | 2197–2211 | 17 | 16 |

Oligonucleotides 14096 and 14097 (SEQ ID NO: 2 and 3) gave greater than 50% inhibition of PKC-α mRNA levels in this assay (at 200 nM dose) and are therefore preferred.

A second set of 15-mer oligonucleotides was synthesized to attempt to optimize the activity observed with ISIS 14096 (SEQ ID NO: 2). Oligonucleotides were targeted to the region of PKC-α mRNA immediately around the target region of ISIS 14096. These compounds were also designed as chimeric oligonucleotides with the first 8 nucleotides at the 5' end being 2'-deoxynucleotides and the remaining 7 nucleotides being 2'-O-methoxyethyl. The intersugar linkages are phosphorothioates throughout and all 2'-O-methoxyethylcytidines have 5-methyl-cytosine bases (5-meC). These compounds are shown in Table 2. Nucleotides shown in bold are 2'-O-methoxyethyl. Activity is expressed as percent inhibition of PKC-α mRNA levels compared to control (no oligo).

therefore preferred. Of these, SEQ ID NO: 18 and 19 gave greater than 70% inhibition of PKC-α expression.

A third set of 15-mer oligonucleotides was synthesized to attempt to optimize the activity observed with ISIS 14097 (SEQ ID NO: 3). Oligonucleotides were targeted to the region of PKC-α mRNA immediately around the target region of ISIS 14097. These compounds were also designed as chimeric oligonucleotides with the first 8 nucleotides at the 5' end being 2'-deoxynucleotides and the remaining 7 nucleotides being 2'-O-methoxyethyl. The intersugar linkages are phosphorothioates throughout and all 2'-O-methoxyethylcytidines have 5-methyl-cytosine bases (5-meC). These compounds are shown in Table 3. Nucleotides shown in bold are 2'-O-methoxyethyl. Activity is expressed as percent inhibition of PKC-α mRNA levels compared to control (no oligo).

TABLE 2

Additional 15-mers targeted to ISIS 14096 target region

| ISIS # | Sequence | % Inhibition | SEQ ID NO: |
|---|---|---|---|
| 14863 | GCGCGATGAATTTGA | 7 | 17 |
| 14864 | AGCGCGCGATGAATT | 79 | 18 |
| 14865 | AGAAGCGCGCGATGA | 71 | 19 |
| 14096 | TGAAGAAGCGCGCGA | 63 | 2 |
| 14868 | GCTTGAAGAAGCGCG | 61 | 20 |
| 14867 | GCTGCTTGAAGAAGC | 0 | 21 |
| 14866 | TGGGCTGCTTGAAGA | 36 | 22 |

Oligonucleotides 14864, 14865, 14096 and 14068 (SEQ ID NO: 18, 19, 2 and 20) gave greater than 50% inhibition of PKC-α mRNA levels in this assay (at 200 nM dose) and are

TABLE 3

Additional 15-mers targeted to ISIS 14097 target region

| ISIS # | Sequence | % Inhibition | SEQ ID NO: |
|---|---|---|---|
| 14857 | TGCTTGCTCCTGGGG | 72 | 23 |
| 14858 | TTGTGCTTGCTCCTG | 34 | 24 |
| 14859 | AACTTGTGCTTGCTC | 73 | 25 |
| 14097 | TTGAACTTGTGCTTG | 59 | 3 |
| 14860 | ATTTTGAACTTGTGC | 53 | 26 |
| 14861 | TGGATTTTGAACTTG | 0 | 27 |
| 14862 | GTGTGGATTTTGAAC | 0 | 28 |

Oligonucleotides 14857, 14859, 14097 and 14860 (SEQ ID NO: 23, 25, 3 and 26) gave greater than 50% inhibition of PKC-α mRNA levels in this assay (at 200 nM dose) and are therefore preferred. Of these, SEQ ID NOs: 23 and 25 gave greater than 70% inhibition of PKC-α expression.

ISIS 14864 (SEQ ID NO: 18) and ISIS 14859 (SEQ ID NO: 25) were compared to ISIS 3521 (5'-GTTCTCGCTGGTGAGTTTCA, SEQ ID NO: 29), the 20-mer phosphorothioate oligodeoxynucleotide which has previously been shown to inhibit PKC-α in vitro and in vivo and which is presently in human clinical trials. Dose response curves were generated for inhibition of PKC-α mRNA levels by these three compounds. $IC_{50}$s were calculated from this assay to be approximately 50 nM for ISIS 14859, 100 nM for ISIS 3521 and 110 nM for ISIS 14864. Thus, the 15-mers 14859 and 14864 are considered to have activity which is comparable to or better than ISIS 3251 for reduction of PKC-α mRNA levels, and are highly preferred.

Example 4

U-87 human glioblastoma cell culture and subcutaneous xenografts into nude mice

ISIS 14864 (SEQ ID NO: 18) was compared to ISIS 3521 (SEQ ID NO: 29) and chimeric 2'-MOE oligonucleotides ISIS 12723 and ISIS 14193, both of which also have SEQ ID NO: 29. These compounds are shown in Table 4. Inter-sugar (backbone) linkages are shown for all compounds since these vary. All 2'-methoxyethyl cytidines are 5-methyl cytidines.

TABLE 4

Additional oligonucleotides targeted to human PKC-α
bold = 2'-O-methoxyethyl; s = P = S linkage,
o = P = O linkage

| ISIS # | Sequence | SEQ ID NO: |
|---|---|---|
| 3521 | GsTsTsCsTsCsGsCsTsGsGsTsGsAsGsTsTsTsCsA | 29 |
| 12723 | GoToToCoToCsGsCsTsGsGsTsGsAsGoToToToCoA | 29 |
| 14193 | GsTsTsCsTsCsGsCsTsGsGsTsGsAsGsTsTsTsCsA | 29 |
| 14864 | AsGsCsGsCsGsCsGsAsTsGsAsAsTsT | 18 |

The U-87 human glioblastoma cell line was obtained from the ATCC (Rockville Md.) and maintained in Iscove's DMEM medium supplemented with heat-inactivated 10% fetal calf serum. Nude mice received 1 mm fragments of U-87 tumor by trocar. Three weeks after implantation, or when tumors reached 100 mm³, oligonucleotide treatment was begun. Mice were injected intraperitoneally with ISIS 3521, ISIS 12723, ISIS 14193 or ISIS 14864, at a dosage of 2 mg/kg, daily for 28 consecutive days or until tumor burden required sacrificing the animals (10% of body weight). Tumor volumes were measured on days 2, 8, 13, 18 and 23. On day 23, ISIS 3521 had reduced tumor volume by 39% compared to saline control. ISIS 12723 had reduced tumor volume by 45%; this compound is therefore preferred. ISIS 14193 and ISIS 14864 had reduced tumor volume by 95% and 96%, respectively, both compared to saline control. These two compounds are therefore highly preferred. By day 28, the number of mice alive in each group were: saline control, 0/8; ISIS 3521, 2/8; ISIS 12723, 1/7; ISIS 14193, 5/7 and ISIS 14864, 5/7. The number of sites that were tumor-free were: ISIS 3521, 0/16; ISIS 12723, 1/14; ISIS 14193, 3/14 and ISIS 14864, 5/14. Tumor growth rates after oligonucleotide treatment were also measured. Compared to saline controls, tumor growth rates (mm³/day) were reduced by 30% by ISIS 3521, 39% by ISIS 12723, 76% by ISIS 14193 and 82% by ISIS 14864.

Thus ISIS 14193 (SEQ ID NO: 29) and ISIS 14864 (SEQ ID NO: 18) are highly preferred embodiments of the present invention.

Example 5

Shortened oligonucleotides targeted to the ISIS 3521 target region

ISIS 3521 (5'-GTTCTCGCTGGTGAGTTTCA, SEQ ID NO: 29) is a 20-mer targeted to the stop codon and 3' untranslated region (nucleotides 2044–2063 of SEQ ID NO: 48; Genbank accession number x52479) of human PKC-α which has been shown to reduce PKC-α expression in vitro and in vivo. Dean et al. (1994) J. Biol. Chem. 269:16416, McGraw et al. (1997) Anti-Cancer Drug Design (1997) 12:315–326. We subsequently deleted one nucleotide from the 3' end of this sequence and either one or two nucleotides from the 5' end. The resulting compounds are shown in Table 5. In some cases these are chimeras of the "gapmer" type with a deoxy gap and 2'-O-propyl wings.

TABLE 5

Chimeric 2'-O-propyl/deoxy P = s oligonucleotides
targeted to PKC-α 3'-UTR
bold = 2'-O-propyl; s = P = S linkage, o = P = O linkage

| OLIGO # | SEQUENCE | SEQ ID NO: |
|---|---|---|
| 6632 | TsTsCs TsCsGs CsTsGs GsTsGs AsGsTs TsTsC | 31 |
| 6653 | TsTsCs TsCsGs CsTsGs GsTsGs AsGsTs TsTsC | 31 |
| 6665 | ToToCo TsCsGs CsTsGs GsTsGs AsGsTo ToToC | 31 |
| 7082 | TsCsTs CsGsCs TsGsGs TsGsAs GsTsTs TsC | 32 |
| 7083 | TsCsTs CsGsCs TsGsGs TsGsAs GsTsTs TsC | 32 |
| 7084 | ToCoTo CsGsCs TsGsGs TsGsAs GsToTo ToC | 32 |

Oligonucleotides 6632 and 6653 reduced PKC-α mRNA levels by approximately 90% and oligonucleotides 7082 and 7083 reduced PKC-α mRNA levels by 65–70%.

Example 6

Oligonucleotide 15-mers targeted to the ISIS 3521 and 3527 target regions

ISIS 3521 (5'-GTTCTCGCTGGTGAGTTTCA, SEQ ID NO: 29) and ISIS 3527 (GAGACCCTGAACAGTTGATC; SEQ ID NO: 30) are 20-mers targeted to the 3' untranslated region of human PKC-α. ISIS 3521 is targeted to nucleotides 2044–2063 of SEQ ID NO: 48 (Genbank accession number x52479), overlapping the stop codon. ISIS 3527 is targeted to nucleotides 2192–2211 of SEQ ID NO: 48. Both have been shown to reduce PKC-α expression. Dean et al. (1994) J. Biol. Chem. 269:16416, McGraw et al. (1997) Anti-Cancer Drug Design (1997) 12:315–326. A series of 15mer oligonucleotides were designed to target the ISIS 3521 and the ISIS 3527 target sites. These are shown in Tables 6 and 7. The ISIS 3521 and 3527 sequences, respectively, are shown to aid in comparing target sequence locations. These compounds were chimeric oligonucleotides with the first 8 nucleotides at the 5' end being 2'-deoxynucleotides and the remaining 7 nucleotides being 2'-O-methoxyethyl. The intersugar linkages are phosphorothioates throughout and all 2'-O-methoxyethylcytidines have 5-methyl-cytosine bases (5-meC). Nucleotides shown in bold are 2'-O-methoxyethyls. Activity is expressed as percent inhibition of PKC-α mRNA levels compared to control (no oligo). Oligonucleotide concentration was 200 nM.

TABLE 6

Inhibition of PKC-α mRNA levels by 15mer oligonucleotides targeted to the ISIS 3521 target region

| ISIS # | Sequence | % Inhibition | SEQ ID NO: |
|---|---|---|---|
| 3521 | GTTCTCGCTGGTGAGTTTCA | | 29 |
| 14881 | GAGTTTCATACTGCA | 12 | 33 |
| 14880 | GTGAGTTTCATACTG | 12 | 34 |
| 14879 | TGGTGAGTTTCATAC | 10 | 35 |
| 14878 | GCTGGTGAGTTTCAT | 20 | 36 |
| 14106 | CGCTGGTGAGTTTCA | 38 | 37 |
| 14877 | TCGCTGGTGAGTTTC | 19 | 38 |
| 14876 | TCTCGCTGGTGAGTT | 31 | 39 |
| 14875 | GTTCTCGCTGGTGAG | 71 | 40 |

ISIS 14875 gave over 70% inhibition of PKC-α expression in this experiment and is therefore preferred.

TABLE 7

Inhibition of PKC-α mRNA levels by 15mer oligonucleotides targeted to the ISIS 3527 target region

| ISIS # | Sequence | % Inhibition | SEQ ID NO: |
|---|---|---|---|
| 3527 | GAGACCCTGAACAGTTGATC | | 30 |
| 14110 | GAGACCCTGAACAGT | 23 | 41 |
| 14869 | GACCCTGAACAGTTG | 23 | 42 |
| 14870 | CCCTGAACAGTTGAT | 24 | 43 |
| 14871 | CTGAACAGTTGATCA | 28 | 44 |
| 14872 | GAACAGTTGATCACA | 3 | 45 |
| 14873 | ACAGTTGATCACATT | 25 | 46 |
| 14874 | AGTTGATCACATTTG | 10 | 47 |

When taken together, these examples demonstrate that, surprisingly, oligonucleotides of reduced length can retain excellent activity for inhibition of PKC expression. Oligonucleotides which demonstrate the ability to reduce PKC expression include ISIS 14096 and 14097 (SEQ ID NO: 2 and 3), 14864, 14865 and 14068 (SEQ ID NO: 18, 19 and 20), 14857, 14859, 14097 and 14860 (SEQ ID NO: 23, 25, 3 and 26) and 14875 (SEQ ID NO: 40). Of these, SEQ ID NO: 18, 19, 23, 25 and 40 gave greater than 70% inhibition of PKC expression.

Example 7

Additional oligonucleotides targeted to human PKC-α

Additional oligonucleotides targeted to the ISIS 3527 region have also been synthesized. The sequences of these compounds, which were made as phosphorothioate oligodeoxynucleotides, are shown in Table 8. Additional short oligonucleotides targeted to other regions of the human PKC-α mRNA are also shown in Table 8. These were also synthesized as phosphorothioate oligodeoxynucleotides. The target site of each oligonucleotide on the human PKC-α mRNA target (Finkenzeller et al., Genbank locus HSPKCA1, accession number X52479)is indicated by the nucleotide number of the 5' most nucleotide on GenBank listing HSPKCA1, accession number X52479, to which the oligonucleotide hybridizes.

TABLE 8

Additional oligonucleotides targeted to human PKC-α

| ISIS # | Sequence | Length | Target site | SEQ ID NO: |
|---|---|---|---|---|
| 3527 | GAGACCCTGAACAGTTGATC | 20 | 2192 | 30 |
| 4921 | AGACCCTGAACA | 12 | 2199 | 49 |
| 4922 | AGAGACCCTGAACAG | 15 | 2198 | 50 |
| 4936 | CCCTGAACAGTTGATC | 16 | 2192 | 51 |
| 4937 | AAGAGAGAGACCCTGA | 16 | 2202 | 52 |
| 4995 | GAGAGACCCTGAACAGTT | 18 | 2196 | 53 |
| 4997 | CTGAACAGTTGATC | 14 | 2192 | 54 |
| 5030 | AAGAGAGAGACCCTGAAC | 18 | 2200 | 55 |
| 5031 | AAGAGAGAGACCCT | 14 | 2204 | 56 |
| 5032 | GAGAGAGACCCTGAACAG | 18 | 2198 | 57 |
| 5046 | GAGACCCTGAACAGTTGA | 18 | 2194 | 58 |
| 5047 | GAGAGACCCTGAACAG | 16 | 2198 | 59 |
| 5048 | GAGACCCTGAACAG | 14 | 2198 | 60 |
| 5061 | AGAGACCCTGAACAGT | 16 | 2197 | 61 |
| 5062 | GAGACCCTGAACAGTT | 16 | 2196 | 62 |
| 6439 | GGGAGGGCTGGG | 12 | 2080 | 63 |
| 6554 | GCGGGGAGGGCT | 12 | 2083 | 64 |
| 6512 | GCCGTGGCCTTA | 12 | 2125 | 65 |
| 6513 | GCCGTGGCCTTAA | 13 | 2124 | 66 |
| 6438 | TTTGTTCTCGCTGG | 14 | 2053 | 67 |
| 6437 | CTTCCACTGCGGGG | 14 | 2089 | 68 |
| 6514 | TCAGACACAAGCCG | 14 | 2133 | 69 |

What is claimed is:

1. An antisense oligonucleotide up to 50 nucleotides in length which is targeted to a nucleic acid encoding a human protein kinase C and which modulates expression of the human protein kinase C, wherein said oligonucleotide comprises SEQ ID NO: 2, 3, 18, 19, 20, 23, 25 or 26.

2. The antisense oligonucleotide of claim 1 which is up to 20 nucleotides in length.

3. The oligonucleotide of claim 1 wherein at least one of the nucleotides contains a modification on the 2' position of the sugar.

4. The antisense oligonucleotide of claim 1 which is a chimeric oligonucleotide.

5. An antisense oligonucleotide consisting of SEQ ID NO: 18.

6. The antisense oligonucleotide of claim 5 wherein each intersugar linkage is a phosphorothioate linkage and wherein the first eight nucleotides at the 5' end of the oligonucleotide are 2'-deoxynucleotides and the remaining seven nucleotides are 2'-O—$CH_2CH_2OCH_3$ nucleotides, and wherein each 2'-O—$CH_2CH_2OCH_3$ cytidine nucleotide is a 5-methyl cytidine.

7. An antisense oligonucleotide consisting of SEQ ID NO: 25.

8. The antisense oligonucleotide of claim 7 wherein each intersugar linkage is a phosphorothioate linkage and wherein the first eight nucleotides at the 5' end of the oligonucleotide are 2'-deoxynucleotides and the remaining seven nucleotides are 2'-O—$CH_2CH_2OCH_3$ nucleotides, and wherein each 2'-O—$CH_2CH_2OCH_3$ cytidine nucleotide is a 5-methyl cytidine.

9. A pharmaceutical composition comprising a therapeutically effective amount of the oligonucleotide of claim 1.

10. A pharmaceutical composition comprising a therapeutically effective amount of the oligonucleotide of claim 5.

11. A pharmaceutical composition comprising a therapeutically effective amount of the oligonucleotide of claim 7.

12. A method of inhibiting human protein kinase C expression in cells comprising contacting the cells with the oligonucleotide of claim 1.

13. A method of inhibiting human protein kinase C expression in cells comprising contacting the cells with the oligonucleotide of claim 5.

14. A method of inhibiting human protein kinase C expression in cells comprising contacting the cells with the oligonucleotide of claim 7.

15. The method of claim 12 wherein the cells are cancer cells.

16. The method of claim 13 wherein the cells are cancer cells.

17. The method of claim 14 wherein the cells are cancer cells.

18. A method of treating a condition associated with expression of protein kinase C comprising administering to a human, or a cell, a tissue, or a bodily fluid thereof, a therapeutically effective amount of the oligonucleotide of claim 1.

19. A method of treating a condition associated with expression of protein kinase C comprising administering to a human, or cells, tissues, or a bodily fluid thereof, a therapeutically effective amount of the oligonucleotide of claim 5.

20. A method of treating a condition associated with expression of protein kinase C comprising administering to a human, or cells, tissues, or a bodily fluid thereof, a therapeutically effective amount of the oligonucleotide of claim 7.

21. The method of claim 18 wherein said condition is an inflammatory or hyperproliferative disorder.

22. The method of claim 19 wherein said condition is an inflammatory or hyperproliferative disorder.

23. The method of claim 20 wherein said condition is an inflammatory or hyperproliferative disorder.

24. The method of claim 21 wherein the condition is cancer or psoriasis.

25. The method of claim 22 wherein the condition is cancer or psoriasis.

26. The method of claim 23 wherein the condition is cancer or psoriasis.

27. An oligonucleotide consisting of SEQ ID NO:40.

28. The oligonucleotide of claim 27 wherein at least one of the nucleotides contains a modification on the 2' position of the sugar.

29. The oligonucleotide of claim 27 which is a chimeric oligonucleotide.

30. A pharmaceutical composition comprising a therapeutically effective amount of the oligonucleotide of claim 27.

31. A method of inhibiting human protein kinase C expression in cells comprising contacting the cells with the oligonucleotide of claim 27.

32. The method of claim 31 wherein the cells are cancer cells.

33. A method of treating a condition associated with expression of protein kinase C comprising administering to a human, or a cell, a tissue, or a bodily fluid thereof, a therapeutically effective amount of the oligonucleotide of claim 27.

34. The method of claim 33 wherein said condition is an inflammatory or hyperproliferative disorder.

35. The method of claim 34 wherein the condition is cancer or psoriasis.

* * * * *

UNITED STATES PATENT AND TRADEMARK OFFICE
CERTIFICATE OF CORRECTION

PATENT NO.   : 6,117,847
DATED        : September 12, 2000
INVENTOR(S)  : Bennett et al.

It is certified that error appears in the above-identified patent and that said Letters Patent is hereby corrected as shown below:

Column 6,
Lines 38 & 39, please delete "O-P-O-CH)." and insert therefor -- O-P-O-$CH_2$). --;
Line 56, please delete "$(CH_2)nCH_3$," and insert therefor -- $(CH_2)_nCH_3$, --;

Column 8,
Line 29, please delete "winginer" and insert therefor -- wingmer --;

Column 17,
Table 1 #14107, please delete "AGQATTCACTTCCAC" and insert therefore -- AGGATTCACTTCCAC --;

Signed and Sealed this

Ninth Day of July, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 69

(2) INFORMATION FOR SEQ ID NO: 1:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 1:

ACCACCTCTT GCTCC                                                          15

(2) INFORMATION FOR SEQ ID NO: 2:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 2:

TGAAGAAGCG CGCGA                                                          15

(2) INFORMATION FOR SEQ ID NO: 3:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 3:

TTGAACTTGT GCTTG                                                          15

(2) INFORMATION FOR SEQ ID NO: 4:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 4:

GCCCCCTCTT CTCAG                                                          15

(2) INFORMATION FOR SEQ ID NO: 5:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 5:

TTCATTCTTG GGATC                                                          15

(2) INFORMATION FOR SEQ ID NO: 6:

(i) SEQUENCE CHARACTERISTICS:
        (A) LENGTH:   15
        (B) TYPE: nucleic acid
        (C) STRANDEDNESS: single (D) TOPOLOGY: linear (xi) SEQUENCE DESCRIPTION: SEQ ID NO: 6:

CATCCACTGG CCGGC                                                                    15

(2) INFORMATION FOR SEQ ID NO: 7:

(i) SEQUENCE CHARACTERISTICS:
            (A) LENGTH:    15
            (B) TYPE: nucleic acid
            (C) STRANDEDNESS: single
            (D) TOPOLOGY: linear (xi) SEQUENCE DESCRIPTION: SEQ ID NO: 7:

TGCCTGAGTT CCATG                                                                    15

(2) INFORMATION FOR SEQ ID NO: 8:

(i) SEQUENCE CHARACTERISTICS:
            (A) LENGTH:    15
            (B) TYPE: nucleic acid
            (C) STRANDEDNESS: single
            (D) TOPOLOGY: linear (xi) SEQUENCE DESCRIPTION: SEQ ID NO: 8:

CAGGATTTTG ATTGC                                                                    15

(2) INFORMATION FOR SEQ ID NO: 9:

(i) SEQUENCE CHARACTERISTICS:
            (A) LENGTH:    15
            (B) TYPE: nucleic acid
            (C) STRANDEDNESS: single
            (D) TOPOLOGY: linear (xi) SEQUENCE DESCRIPTION: SEQ ID NO: 9:

TCCGATGGAA ATCTC                                                                    15

(2) INFORMATION FOR SEQ ID NO: 10:

(i) SEQUENCE CHARACTERISTICS:
            (A) LENGTH:    15
            (B) TYPE: nucleic acid
            (C) STRANDEDNESS: single
            (D) TOPOLOGY: linear (xi) SEQUENCE DESCRIPTION: SEQ ID NO: 10:

ACTCCATCCA TCATG                                                                    15

(2) INFORMATION FOR SEQ ID NO: 11:

(i) SEQUENCE CHARACTERISTICS:
            (A) LENGTH:    15
            (B) TYPE: nucleic acid
            (C) STRANDEDNESS: single
            (D) TOPOLOGY: linear (xi) SEQUENCE DESCRIPTION: SEQ ID NO: 11:

GCATGCTCTC TCACG                                                                    15

(2) INFORMATION FOR SEQ ID NO: 12:

(i) SEQUENCE CHARACTERISTICS:
            (A) LENGTH:    15
            (B) TYPE: nucleic acid
            (C) STRANDEDNESS: single
            (D) TOPOLOGY: linear (xi) SEQUENCE DESCRIPTION: SEQ ID NO: 12:

CGCTGGTGAG TTTCA                                                15

(2) INFORMATION FOR SEQ ID NO: 13:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 13:

AGGATTCACT TCCAC                                                15

(2) INFORMATION FOR SEQ ID NO: 14:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 14:

CCGTGGCCTT AAAAT                                                15

(2) INFORMATION FOR SEQ ID NO: 15:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 15:

CCCTACAATT TTCAG                                                15

(2) INFORMATION FOR SEQ ID NO: 16:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 16:

GAGACCCTGA ACAGT                                                15

(2) INFORMATION FOR SEQ ID NO: 17:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 17:

GCGCGATGAA TTTGA                                                15

(2) INFORMATION FOR SEQ ID NO: 18:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 18:

AGCGCGCGAT GAATT                                              15

(2) INFORMATION FOR SEQ ID NO: 19:

(i) SEQUENCE CHARACTERISTICS:
        (A) LENGTH:    15
        (B) TYPE: nucleic acid
        (C) STRANDEDNESS: single
        (D) TOPOLOGY: linear (xi) SEQUENCE DESCRIPTION: SEQ ID NO: 19:

AGAAGCGCGC GATGA                                              15

(2) INFORMATION FOR SEQ ID NO: 20:

(i) SEQUENCE CHARACTERISTICS:
        (A) LENGTH:    15
        (B) TYPE: nucleic acid
        (C) STRANDEDNESS: single
        (D) TOPOLOGY: linear (xi) SEQUENCE DESCRIPTION: SEQ ID NO: 20:

GCTTGAAGAA GCGCG                                              15

(2) INFORMATION FOR SEQ ID NO: 21:

(i) SEQUENCE CHARACTERISTICS:
        (A) LENGTH:    15
        (B) TYPE: nucleic acid
        (C) STRANDEDNESS: single
        (D) TOPOLOGY: linear (xi) SEQUENCE DESCRIPTION: SEQ ID NO: 21:

GCTGCTTGAA GAAGC                                              15

(2) INFORMATION FOR SEQ ID NO: 22:

(i) SEQUENCE CHARACTERISTICS:
        (A) LENGTH:    15
        (B) TYPE: nucleic acid
        (C) STRANDEDNESS: single
        (D) TOPOLOGY: linear (xi) SEQUENCE DESCRIPTION: SEQ ID NO: 22:

TGGGCTGCTT GAAGA                                              15

(2) INFORMATION FOR SEQ ID NO: 23:

(i) SEQUENCE CHARACTERISTICS:
        (A) LENGTH:    15
        (B) TYPE: nucleic acid
        (C) STRANDEDNESS: single
        (D) TOPOLOGY: linear (xi) SEQUENCE DESCRIPTION: SEQ ID NO: 23:

TGCTTGCTCC TGGGG                                              15

(2) INFORMATION FOR SEQ ID NO: 24:

(i) SEQUENCE CHARACTERISTICS:
        (A) LENGTH:    15
        (B) TYPE: nucleic acid
        (C) STRANDEDNESS: single
        (D) TOPOLOGY: linear (xi) SEQUENCE DESCRIPTION: SEQ ID NO: 24:

TTGTGCTTGC TCCTG                                                    15

(2) INFORMATION FOR SEQ ID NO: 25:

(i) SEQUENCE CHARACTERISTICS:
        (A) LENGTH:    15
        (B) TYPE: nucleic acid
        (C) STRANDEDNESS: single
        (D) TOPOLOGY: linear (xi) SEQUENCE DESCRIPTION: SEQ ID NO: 25:

AACTTGTGCT TGCTC                                                    15

(2) INFORMATION FOR SEQ ID NO: 26:

(i) SEQUENCE CHARACTERISTICS:
        (A) LENGTH:    15
        (B) TYPE: nucleic acid
        (C) STRANDEDNESS: single
        (D) TOPOLOGY: linear (xi) SEQUENCE DESCRIPTION: SEQ ID NO: 26:

ATTTTGAACT TGTGC                                                    15

(2) INFORMATION FOR SEQ ID NO: 27:

(i) SEQUENCE CHARACTERISTICS:
        (A) LENGTH:    15
        (B) TYPE: nucleic acid
        (C) STRANDEDNESS: single
        (D) TOPOLOGY: linear (xi) SEQUENCE DESCRIPTION: SEQ ID NO: 27:

TGGATTTTGA ACTTG                                                    15

(2) INFORMATION FOR SEQ ID NO: 28:

(i) SEQUENCE CHARACTERISTICS:
        (A) LENGTH:    15
        (B) TYPE: nucleic acid
        (C) STRANDEDNESS: single
        (D) TOPOLOGY: linear (xi) SEQUENCE DESCRIPTION: SEQ ID NO: 28:

GTGTGGATTT TGAAC                                                    15

(2) INFORMATION FOR SEQ ID NO: 29:

(i) SEQUENCE CHARACTERISTICS:
        (A) LENGTH:    20
        (B) TYPE: nucleic acid
        (C) STRANDEDNESS: single
        (D) TOPOLOGY: linear (xi) SEQUENCE DESCRIPTION: SEQ ID NO: 29:

GTTCTCGCTG GTGAGTTTCA                                               20

(2) INFORMATION FOR SEQ ID NO: 30:

(i) SEQUENCE CHARACTERISTICS:
        (A) LENGTH:    20
        (B) TYPE: nucleic acid
        (C) STRANDEDNESS: single
        (D) TOPOLOGY: linear (xi) SEQUENCE DESCRIPTION: SEQ ID NO: 30:

```
GAGACCCTGA ACAGTTGATC                                              20

(2) INFORMATION FOR SEQ ID NO: 31:

(i) SEQUENCE CHARACTERISTICS:
         (A) LENGTH:   18
         (B) TYPE: nucleic acid
         (C) STRANDEDNESS: single
         (D) TOPOLOGY: linear (xi) SEQUENCE DESCRIPTION: SEQ ID NO: 31:

TTCTCGCTGG TGAGTTTC                                                18

(2) INFORMATION FOR SEQ ID NO: 32:

(i) SEQUENCE CHARACTERISTICS:
         (A) LENGTH:   17
         (B) TYPE: nucleic acid
         (C) STRANDEDNESS: single
         (D) TOPOLOGY: linear (xi) SEQUENCE DESCRIPTION: SEQ ID NO: 32:

TCTCGCTGGT GAGTTTC                                                 17

(2) INFORMATION FOR SEQ ID NO: 33:

(i) SEQUENCE CHARACTERISTICS:
         (A) LENGTH:   15
         (B) TYPE: nucleic acid
         (C) STRANDEDNESS: single
         (D) TOPOLOGY: linear (xi) SEQUENCE DESCRIPTION: SEQ ID NO: 33:

GAGTTTCATA CTGCA                                                   15

(2) INFORMATION FOR SEQ ID NO: 34:

(i) SEQUENCE CHARACTERISTICS:
         (A) LENGTH:   15
         (B) TYPE: nucleic acid
         (C) STRANDEDNESS: single
         (D) TOPOLOGY: linear (xi) SEQUENCE DESCRIPTION: SEQ ID NO: 34:

GTGAGTTTCA TACTG                                                   15

(2) INFORMATION FOR SEQ ID NO: 35:

(i) SEQUENCE CHARACTERISTICS:
         (A) LENGTH:   15
         (B) TYPE: nucleic acid
         (C) STRANDEDNESS: single
         (D) TOPOLOGY: linear (xi) SEQUENCE DESCRIPTION: SEQ ID NO: 35:

TGGTGAGTTT CATAC                                                   15

(2) INFORMATION FOR SEQ ID NO: 36:

(i) SEQUENCE CHARACTERISTICS:
         (A) LENGTH:   15
         (B) TYPE: nucleic acid
         (C) STRANDEDNESS: single
         (D) TOPOLOGY: linear (xi) SEQUENCE DESCRIPTION: SEQ ID NO: 36:

GCTGGTGAGT TTCAT                                                   15
```

-continued (2) INFORMATION FOR SEQ ID NO: 37:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 37:

CGCTGGTGAG TTTCA                              15

(2) INFORMATION FOR SEQ ID NO: 38:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 38:

TCGCTGGTGA GTTTC                              15

(2) INFORMATION FOR SEQ ID NO: 39:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 39:

TCTCGCTGGT GAGTT                              15

(2) INFORMATION FOR SEQ ID NO: 40:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 40:

GTTCTCGCTG GTGAG                              15

(2) INFORMATION FOR SEQ ID NO: 41:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 41:

GAGACCCTGA ACAGT                              15

(2) INFORMATION FOR SEQ ID NO: 42:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 42:

GACCCTGAAC AGTTG                              15

(2) INFORMATION FOR SEQ ID NO: 43:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 43:

```
CCCTGAACAG TTGAT                                                    15
```

(2) INFORMATION FOR SEQ ID NO: 44:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 44:

```
CTGAACAGTT GATCA                                                    15
```

(2) INFORMATION FOR SEQ ID NO: 45:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 45:

```
GAACAGTTGA TCACA                                                    15
```

(2) INFORMATION FOR SEQ ID NO: 46:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 46:

```
ACAGTTGATC ACATT                                                    15
```

(2) INFORMATION FOR SEQ ID NO: 47:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 47:

```
AGTTGATCAC ATTTG                                                    15
```

(2) INFORMATION FOR SEQ ID NO: 48:

(i) SEQUENCE CHARACTERISTICS:
        (A) LENGTH: 2244
        (B) TYPE: nucleic acid
        (C) STRANDEDNESS: single
        (D) TOPOLOGY: linear (xi) SEQUENCE DESCRIPTION: SEQ ID NO: 48:

```
GGAGCAAGAG GTGGTTGGGG GGGGACCATG GCTGACGTTT TCCCGGGCAA              50
CGACTCCACG GCGTCTCAGG ACGTGGCCAA CCGCTTCGCC CGCAAAGGGG             100
```

-continued

```
CGCTGAGGCA GAAGAACGTG CACGAGGTGA AGGACCACAA ATTCATCGCG          150

CGCTTCTTCA AGCAGCCCAC CTTCTGCAGC CACTGCACCG ACTTCATCTG          200

GGGGTTTGGG AAACAAGGCT TCCAGTGCCA AGTTTGCTGT TTTGTGGTCC          250

ACAAGAGGTG CCATGAATTT GTTACTTTTT CTTGTCCGGG TGCGGATAAG          300

GGACCCGACA CTGATGACCC CAGGAGCAAG CACAAGTTCA AAATCCACAC          350

TTACGGAAGC CCCACCTTCT GCGATCACTG TGGGTCACTG CTCTATGGAC          400

TTATCCATCA AGGGATGAAA TGTGACACCT GCGATATGAA CGTTCACAAG          450

CAATGCGTCA TCAATGTCCC CAGCCTCTGC GGAATGGATC ACACTGAGAA          500

GAGGGGCGG ATTTACCTAA AGGCTGAGGT TGCTGATGAA AAGCTCCATG           550

TCACAGTACG AGATGCAAAA AATCTAATCC CTATGGATCC AAACGGGCTT          600

TCAGATCCTT ATGTGAAGCT GAAACTTATT CCTGATCCCA AGAATGAAAG          650

CAAGCAAAAA ACCAAAACCA TCCGCTCCAC ACTAAATCCG CAGTGGAATG          700

AGTCCTTTAC ATTCAAATTG AAACCTTCAG ACAAAGACCG ACGACTGTCT          750

GTAGAAATCT GGGACTGGGA TCGAACAACA AGGAATGACT TCATGGGATC          800

CCTTTCCTTT GGAGTTTCGG AGCTGATGAA GATGCCGGCC AGTGGATGGT          850

ACAAGTTGCT TAACCAAGAA GAAGGTGAGT ACTACAACGT ACCCATTCCG          900

GAAGGGACG AGGAAGGAAA CATGGAACTC AGGCAGAAAT TCGAGAAAGC           950

CAAACTTGGC CCTGCTGGCA ACAAAGTCAT CAGTCCCTCT GAAGACAGGA         1000

AACAACCTTC CAACAACCTT GACCGAGTGA AACTCACGGA CTTCAATTTC         1050

CTCATGGTGT TGGGAAAGGG GAGTTTTGGA AAGGTGATGC TTGCCGACAG         1100

GAAGGGCACA GAAGAACTGT ATGCAATCAA AATCCTGAAG AAGGATGTGG         1150

TGATTCAGGA TGATGACGTG GAGTGCACCA TGGTAGAAAA GCGAGTCTTG         1200

GCCCTGCTTG ACAAACCCCC GTTCTTGACG CAGCTGCACT CCTGCTTCCA         1250

GACAGTGGAT CGGCTGTACT TCGTCATGGA ATATGTCAAC GGTGGGGACC         1300

TCATGTACCA CATTCAGCAA GTAGGAAAAT TTAAGGAACC ACAAGCAGTA         1350

TTCTATGCGG CAGAGATTTC CATCGGATTG TTCTTTCTTC ATAAAAGAGG         1400

AATCATTTAT AGGGATCTGA AGTTAGATAA CGTCATGTTG GATTCAGAAG         1450

GACATATCAA AATTGCTGAC TTTGGGATGT GCAAGGAACA CATGATGGAT         1500

GGAGTCACGA CCAGGACCTT CTGTGGGACT CCAGATTATA TCGCCCCAGA         1550

GATAATCGCT TATCAGCCGT ATGGAAAATC TGTGGACTGG TGGGCCTATG         1600

GCGTCCTGTT GTATGAAATG CTTGCCGGGC AGCCTCCATT TGATGGTGAA         1650

GATGAAGACG AGCTATTTCA GTCTATCATG GAGCACAACG TTTCCTATCC         1700

AAAATCCTTG TCCAAGGAGG CTGTTTCTAT CTGCAAAGGA CTGATGACCA         1750

AACACCCAGC CAAGCGGCTG GGCTGTGGGC CTGAGGGGA GAGGGACGTG          1800

AGAGAGCATG CCTTCTTCCG GAGGATCGAC TGGGAAAACT GGAGAACAGG         1850

GAGATCCAGC CACCATTCAA GCCCAAAGTG TGTGGCAAAG GAGCAGAGAA         1900

CTTTGACAAG TTCTTCACAC GAGGACAGCC CGTCTTAACA CCACCTGATC         1950

AGCTGGTTAT TGCTAACATA GACCAGTCTG ATTTTGAAGG GTTCTCGTAT         2000

GTCAACCCCC AGTTTGTGCA CCCCATCTTA CAGAGTGCAG TATGAAACTC         2050
```

```
ACCAGCGAGA ACAAACACCT CCCCAGCCCC CAGCCCTCCC CGCAGTGGAA        2100

GTGAATCCTT AACCCTAAAA TTTTAAGGCC ACGGCTTGTG TCTGATTCCA        2150

TATGGAGGCC TGAAAATTGT AGGGTTATTA GTCCAAATGT GATCAACTGT        2200

TCAGGGTCTC TCTCTTACAA CCAAGAACAT TATCTTAGTG GAAG              2244

(2) INFORMATION FOR SEQ ID NO: 49:

(i) SEQUENCE CHARACTERISTICS:
        (A) LENGTH:   12
        (B) TYPE: nucleic acid
        (C) STRANDEDNESS: single
        (D) TOPOLOGY: linear (xi) SEQUENCE DESCRIPTION: SEQ ID NO: 49:

AGACCCTGAA CA                                                  12

(2) INFORMATION FOR SEQ ID NO: 50:

(i) SEQUENCE CHARACTERISTICS:
        (A) LENGTH:   15
        (B) TYPE: nucleic acid
        (C) STRANDEDNESS: single
        (D) TOPOLOGY: linear (xi) SEQUENCE DESCRIPTION: SEQ ID NO: 50:

AGAGACCCTG AACAG                                               15

(2) INFORMATION FOR SEQ ID NO: 51:

(i) SEQUENCE CHARACTERISTICS:
        (A) LENGTH:   16
        (B) TYPE: nucleic acid
        (C) STRANDEDNESS: single
        (D) TOPOLOGY: linear (xi) SEQUENCE DESCRIPTION: SEQ ID NO: 51:

CCCTGAACAG TTGATC                                              16

(2) INFORMATION FOR SEQ ID NO: 52:

(i) SEQUENCE CHARACTERISTICS:
        (A) LENGTH:   16
        (B) TYPE: nucleic acid
        (C) STRANDEDNESS: single
        (D) TOPOLOGY: linear (xi) SEQUENCE DESCRIPTION: SEQ ID NO: 52:

AAGAGAGAGA CCCTGA                                              16

(2) INFORMATION FOR SEQ ID NO: 53:

(i) SEQUENCE CHARACTERISTICS:
        (A) LENGTH:   18
        (B) TYPE: nucleic acid
        (C) STRANDEDNESS: single
        (D) TOPOLOGY: linear (xi) SEQUENCE DESCRIPTION: SEQ ID NO: 53:

GAGAGACCCT GAACAGTT                                            18

(2) INFORMATION FOR SEQ ID NO: 54:

(i) SEQUENCE CHARACTERISTICS:
        (A) LENGTH:   14
        (B) TYPE: nucleic acid
```

```
        (C) STRANDEDNESS: single
        (D) TOPOLOGY: linear (xi) SEQUENCE DESCRIPTION: SEQ ID NO: 54:

CTGAACAGTT GATC                                                           14

(2) INFORMATION FOR SEQ ID NO: 55:

(i) SEQUENCE CHARACTERISTICS:
        (A) LENGTH:   18
        (B) TYPE: nucleic acid
        (C) STRANDEDNESS: single
        (D) TOPOLOGY: linear (xi) SEQUENCE DESCRIPTION: SEQ ID NO: 55:

AAGAGAGAGA CCCTGAAC                                                       18

(2) INFORMATION FOR SEQ ID NO: 56:

(i) SEQUENCE CHARACTERISTICS:
        (A) LENGTH:   14
        (B) TYPE: nucleic acid
        (C) STRANDEDNESS: single
        (D) TOPOLOGY: linear (xi) SEQUENCE DESCRIPTION: SEQ ID NO: 56:

AAGAGAGAGA CCCT                                                           14

(2) INFORMATION FOR SEQ ID NO: 57:

(i) SEQUENCE CHARACTERISTICS:
        (A) LENGTH:   18
        (B) TYPE: nucleic acid
        (C) STRANDEDNESS: single
        (D) TOPOLOGY: linear (xi) SEQUENCE DESCRIPTION: SEQ ID NO: 57:

GAGAGAGACC CTGAACAG                                                       18

(2) INFORMATION FOR SEQ ID NO: 58:

(i) SEQUENCE CHARACTERISTICS:
        (A) LENGTH:   18
        (B) TYPE: nucleic acid
        (C) STRANDEDNESS: single
        (D) TOPOLOGY: linear (xi) SEQUENCE DESCRIPTION: SEQ ID NO: 58:

GAGACCCTGA ACAGTTGA                                                       18

(2) INFORMATION FOR SEQ ID NO: 59:

(i) SEQUENCE CHARACTERISTICS:
        (A) LENGTH:   16
        (B) TYPE: nucleic acid
        (C) STRANDEDNESS: single
        (D) TOPOLOGY: linear (xi) SEQUENCE DESCRIPTION: SEQ ID NO: 59:

GAGAGACCCT GAACAG                                                         16

(2) INFORMATION FOR SEQ ID NO: 60:

(i) SEQUENCE CHARACTERISTICS:
        (A) LENGTH:   14
        (B) TYPE: nucleic acid
        (C) STRANDEDNESS: single
```

(D) TOPOLOGY: linear (xi) SEQUENCE DESCRIPTION: SEQ ID NO: 60:

GAGACCCTGA ACAG                                                            14

(2) INFORMATION FOR SEQ ID NO: 61:

(i) SEQUENCE CHARACTERISTICS:
            (A) LENGTH:    16
            (B) TYPE: nucleic acid
            (C) STRANDEDNESS: single
            (D) TOPOLOGY: linear (xi) SEQUENCE DESCRIPTION: SEQ ID NO: 61:

AGAGACCCTG AACAGT                                                          16

(2) INFORMATION FOR SEQ ID NO: 62:

(i) SEQUENCE CHARACTERISTICS:
            (A) LENGTH:    16
            (B) TYPE: nucleic acid
            (C) STRANDEDNESS: single
            (D) TOPOLOGY: linear (xi) SEQUENCE DESCRIPTION: SEQ ID NO: 62:

GAGACCCTGA ACAGTT                                                          16

(2) INFORMATION FOR SEQ ID NO: 63:

(i) SEQUENCE CHARACTERISTICS:
            (A) LENGTH:    12
            (B) TYPE: nucleic acid
            (C) STRANDEDNESS: single
            (D) TOPOLOGY: linear (xi) SEQUENCE DESCRIPTION: SEQ ID NO: 63:

GGGAGGGCTG GG                                                              12

(2) INFORMATION FOR SEQ ID NO: 64:

(i) SEQUENCE CHARACTERISTICS:
            (A) LENGTH:    12
            (B) TYPE: nucleic acid
            (C) STRANDEDNESS: single
            (D) TOPOLOGY: linear (xi) SEQUENCE DESCRIPTION: SEQ ID NO: 64:

GCGGGGAGGG CT                                                              12

(2) INFORMATION FOR SEQ ID NO: 65:

(i) SEQUENCE CHARACTERISTICS:
            (A) LENGTH:    12
            (B) TYPE: nucleic acid
            (C) STRANDEDNESS: single
            (D) TOPOLOGY: linear (xi) SEQUENCE DESCRIPTION: SEQ ID NO: 65:

GCCGTGGCCT TA                                                              12

(2) INFORMATION FOR SEQ ID NO: 66:

(i) SEQUENCE CHARACTERISTICS:
            (A) LENGTH:    13
            (B) TYPE: nucleic acid
            (C) STRANDEDNESS: single
            (D) TOPOLOGY: linear

```
        (xi) SEQUENCE DESCRIPTION: SEQ ID NO: 66:

GCCGTGGCCT TAA                                                          13

(2) INFORMATION FOR SEQ ID NO: 67:

(i) SEQUENCE CHARACTERISTICS:
        (A) LENGTH:    14
        (B) TYPE: nucleic acid
        (C) STRANDEDNESS: single
        (D) TOPOLOGY: linear (xi) SEQUENCE DESCRIPTION: SEQ ID NO: 67:

TTTGTTCTCG CTGG                                                         14

(2) INFORMATION FOR SEQ ID NO: 68:

(i) SEQUENCE CHARACTERISTICS:
        (A) LENGTH:    14
        (B) TYPE: nucleic acid
        (C) STRANDEDNESS: single
        (D) TOPOLOGY: linear (xi) SEQUENCE DESCRIPTION: SEQ ID NO: 68:

CTTCCACTGC GGGG                                                         14

(2) INFORMATION FOR SEQ ID NO: 69:

(i) SEQUENCE CHARACTERISTICS:
        (A) LENGTH:    14
        (B) TYPE: nucleic acid
        (C) STRANDEDNESS: single
        (D) TOPOLOGY: linear (xi) SEQUENCE DESCRIPTION: SEQ ID NO: 69:

TCAGACACAA GCCG                                                         14
```